United States Patent [19]

McRae

[11] Patent Number: Plant 6,323

[45] Date of Patent: Oct. 4, 1988

[54] LILY PLANT NAMED DAYSTAR

[75] Inventor: Edward A McRae, Boring, Oreg.

[73] Assignee: Melridge Inc., Aurora, Oreg.

[21] Appl. No.: 923,057

[22] Filed: Oct. 24, 1986

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Charles W. Rummler

[57] ABSTRACT

A new variety of hybrid lily plant bearing large clusters of flowers of excellent form particularly distinguished by their pale cream yellow/soft pink bicolor pattern and by their lack of any spotting. The flowers of this new plant are characterized by their long persistence both on the plant and as cut flowers and with the unusual color combination are completely new in the upright Asiatic division of lilies suited to forcing and to mass commercial cultivation. This plant is highly resistant to disease and shows high tolerance of virus, it is an excellent garden plant, and its bulbs may be precooled and forced for cut flower production. The clone is vigorous and is an excellent grower and propagator.

1 Drawing Sheet

BACKGROUND OF THE INVENTION

This new Asiatic lily variety originated as a seedling selected from a group of seedlings resulting from my crossing at Sandy, Oreg., the clonal cultivar 'Connecticut Queen' (unpatented) as the seed parent and the clonal cultivar 'Sunrise' (unpatented) as the pollen parent. This particular seedling was selected by me because of its very unusual flower coloration of pale yellow and soft pink with a complete lack of any spotting. Asexual propagation of this selected seedling was done by me and under my direction at Sandy, Oreg., by bulb scale propagation, with such excellent results that further propagation was carried on under my direction through several successive generations both by bulb scale propagation and by natural propagation from bulblets, which demonstrated that the novel and distinctive characteristics of this new plant would hold true from generation to generation under asexual propagation and appeared to be firmly fixed. This extended propagation of this new variety shows that it possesses all of the desired characteristics of excellence of flower form, color and habit with flowers of medium size produced profusely in raceme arrangement on a single stem, the clone being a vigorous and good grower and propagator and well suited to forcing out of season when the bulbs are dug at the appropriate time and properly precooled; October-dug bulbs, properly precooled and potted in January, will flower under glass in western Oregon with no supplementary lighting and at moderate greenhouse temperatures in an average of 75 to 80 days, as observed at Sandy, Oreg.

DESCRIPTION OF THE DRAWING

This new variety of lily plant is illustrated in the accompanying photographic drawing, the upper view of which shows a number of the flowers in full bloom together with buds, and the lower view shows a full face view of a mature flower of this variety illustrating its novel characteristics, the colors shown being as close to those specified as is reasonably possible to obtain by means of conventional photographic procedures.

DESCRIPTION OF THE NEW VARIETY

The following is a detailed description of my new variety of Asiatic lily plant with nomenclature according to The International Lily Register (Royal Horticultural Society of London, Second Edition, 1969) and with color designations according to the color chart of The Royal Horticultural Society published in 1966.

THE PLANT

Origin: Seedling.

Parentage:

*Seed parent.*—Lilium 'Connecticut Queen' (unpatented).

*Pollen parent.*—Lilium 'Sunrise' (unpatented).

Classification:

*Horticultural.*—Division I-A, Upright Asiatic Hybrid Lily, according to The Horticultural Classification of Lilies by The Royal Horticultural Society.

*Commercial.*—Hybrid Lily cultivar.

Form: Single stem, erect and stately.

Height: About 70 to 90 cm. from bulbs of about 15 to 18 cm. in circumference.

Growth: Upright and vigorous.

Foliage:

*Quantity.*—Abundant.

*Leaf size.*—About 8 to 10 cm. long and about 5 to 12 mm. wide.

*Leaf shape.*—Lanceolate with acuminate tip.

*Texture.*—Leathery.

*Aspect.*—Glossy and lightly pubescent.

*Color.*—Medium green and somewhat lighter on the under side.

Bulbs:

*Size.*—Variable, ranging up to 25 cm. in circumferece in commercial use.

*Color.*—White.

THE BUD

Form: Long oval with rounded base and acute apex.

Size: About 8 to 9 cm. long and about 5 cm. in circumference, just prior to opening.

Opening rate: The buds open slowly, taking about one hour in response to morning light.

Color: Yellow green, 154C/D, underlaid with 18B at the base of the bud and 36B at the apex.

Peduncle:

*Length.*—Averaging about 4 to 6 cm.; but the length may increase if light levels are too low or if the bulbs have been improperly stored prior to forcing.

*Color.*—Medium green with light plum overlay.

THE FLOWER

Blooming habit: Once annually and profusely in midseason for Asiatic lilies.

Size: Medium for Asiatic hybrids, the diameter averaging about 12 to 14 cm.

Borne: In a single raceme comprising 8 to 10 buds from a bulb about 14 cm. in circumference.

Shape: Cup-shaped when bloom first opens and becoming flattened as the tepals recurve during the second day.

Tepalage:

*Number.*—Six.

*Arrangement.*—Hexagonal and imbricated.

*Shape.*—Generally elliptical with obtuse apexes.

*Size.*—Outer tepals, about 2 to 2½ cm. wide with the inner tepals being about 3 cm. wide.

*Appearance.*—Bicolored with the central portion of the tepals being yellow, 8C to 9D, which extends toward the margins and tip where it is there overlaid with a soft pink pigmentation that deepens as it approaches the tepal tips, the pink coloration overlaying the cream yellow thereby creating a soft peach-pink visual effect; at the tepal tips, the color is red, 38B-C.

*Color changes.*—The peach-pink color is affected by temperature and light levels; decreasing with very high temperatures and with low light. The nectary furrow is the same color as the tepal tips.

*Spotting.*—The tepals are wholly unspotted.

Pedicel:

*Length.*—About 6 cm., in average.

*Form.*—Sturdy and ascending up to about 45° from the horizontal and bearing occasional secondary buds.

*Color.*—Medium green with light plum overlay.

Appearance: The flower is shiny.

Persistence: The tepals stay on the stems for about three weeks.

Fragrance: None.

Lasting quality: The flowers are long lasting both on the plant and as a cut flower.

Disease resistance: The flower and plant are resistant to diseases and in particular, they are resistant to Botrytis blight and Fusarium bulb rot.

THE REPRODUCTIVE ORGANS

Stamens:

*Number.*—Six.

*Arrangement.*—Typical of the genus Lilium.

*Anthers (dehisced) and pollen.*—Greyed orange, 167A.

*Filaments.*—Length: About 5 cm. Color: Soft yellow, 6D.

Pistils:

*Number.*—One.

*Style.*—Length: About 5 cm.

*Stigma.*—Size: Small. Color: Soft green.

Character of ovary: Typical of genus Lilium.

THE FRUIT

Fertility: The fruit is fertile.

Shape: Ovoid

Color at maturity: Soft brown, sometimes overlaid with soft plum.

This hybrid lily plant most nearly resembles the variety 'Connecticut Queen' but it is distinguished by having a soft peach-pink suffusion reaching to the tepal tips and having a soft peach-pink "sliver" of color along the nectary furrows. This variety is reliable for forcing out of season, unlike 'Connecticut Queen'.

I claim:

1. The new and distinctive variety of Asiatic hybrid lily plant, substantially as herein shown and described, characterized by its unique color pattern of soft cream yellow with soft peach-pink tepal tips, a complete lack of spots, and the excellence of its flower form; its vigorous growth habit and rapid natural propagation; and its excellent versatility both as a garden plant and as a flower produced from precooled bulbs forced out of season under glass.

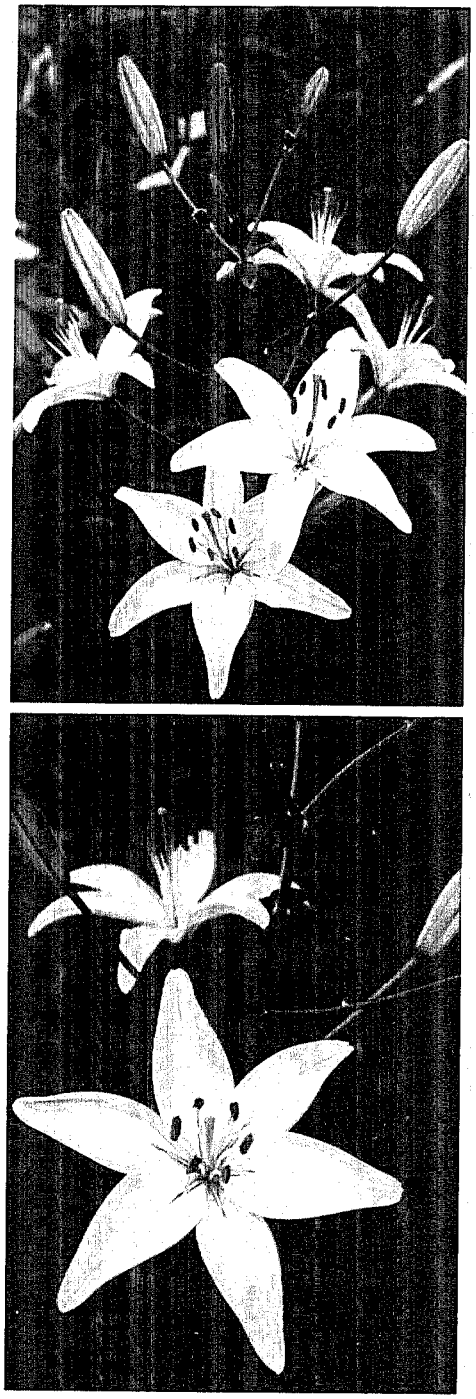

* * * * *